United States Patent [19]

Calub

[11] Patent Number: 4,764,643
[45] Date of Patent: Aug. 16, 1988

[54] ROUTE TO HYBRID RICE PRODUCTION
[75] Inventor: Alfonso G. Calub, East Bernard, Tex.
[73] Assignee: Ring Around Products, Inc., Prattville, Ala.
[21] Appl. No.: 1,227
[22] Filed: Jan. 6, 1987
[51] Int. Cl.$^4$ .............................. A01G 1/00
[52] U.S. Cl. .......................... 800/1; 47/58; 47/DIG. 1
[58] Field of Search ............... 47/58, DIG. 1; 800/1
[56] References Cited

U.S. PATENT DOCUMENTS 3,842,538 10/1974 Barabas .
4,305,225 12/1981 Yuan .
4,351,130 9/1982 Rutger et al. .

OTHER PUBLICATIONS

"Hybrid Rice–Problems and Potential", by J. W. Stansel and J. P. Craigmiles, Rice Journal, vol. 69, No. 5, pp. 14 to 15, and 46 (1966).
"Outlook for Hybrid Rice in the USA", by H. L. Carnahan, J. R. Erikson, S. T. Tseng, and J. N. Rutger, Rice Breeding, International Rice Research Institute, Laguna, Philippines, pp. 603 to 607 (1972).
"Outlook for Hybrid Rice in India", by M. S. Swaminathan, E. A. Siddiq, and S. D. Sharma, Rice Breeding, International Rice Research Institute, Laguna, Philippines, pp. 609 to 613 (1972).
"Current Status and Future Prospects for Breeding Hybrid Rice and Wheat", S. S. Virmani and Jan B. Edwards, *Advances in Agronomy*, vol. 36, pp. 145 to 214 (1983).
"A Concise Course in Hybrid Rice", by Long P. Yuan, Hunan Science and Technology Publishers, Hunan, China, pp. 1 to 168 (1985).
"Current Status of Hybrid Rice Research and Development", by L. P. Yuan and S. S. Virmani, International Symposium on Hybrid Rice, Changsha, Hunan, China, pp. 1 to 16 plus tables (1986).
"Pollination and the Flower of Rice", by Pedro A. Rodrigo, *Phil. Agric., vol. 14, pp. 155 to 171 (1925).*
"Variations in the Breeding Systems of a Wild Rice", "Variation in Anther and Stigma Characteristics in Rice", by K. S. Parmar, E. A. Siddiq and M. S. Swaminathan, *Indian J. Genet.*, vol. 39, pp. 551–559 (1979).
"Stigma Exsertion in Rice and Its Influence on Seed Set of Male Sterile Plants", by Bert J. Hoff and Mercedes De La Torre, Proc. 19th RTWG, Hot Springs Ark., p. 21 (1982).
"Stigma Receptivity of Some Cytoplasmic Male-Sterile Lines of Rice," by S. S. Virmani and Zhong-He Tan, IRRN 7:6, pp. 3–4 (1982).
"Local Indica Rice Varieties With Desirable Floral Traits Influencing Outcrossing", H. C. Sarkar and N. M. Miah, IRRN 8:5, pp. 3–4 (1983).
"Outcrossing Mechanisms and Hybrid Seed Production", Abstracts, Session V, International Symposium on Hybrid Rice, Changsha, Hunan, China, pp. 1 to 6, 6–10 Oct. 1986.

(List continued on next page.)

Primary Examiner—Robert E. Bagwill
Attorney, Agent, or Firm—Burns, Doane, Swecker & Mathis

[57] ABSTRACT

An improved procedure for forming $F_1$ hybrid *Oryza sativa* plants (i.e., hybrid rice plants of the first filial generation) is provided which is capable of being economically implemented on a commercial scale. Plants of the seed and pollen parents each possess a combination of characteristics (as described) which readily facilitate cross-pollination in the absence of the application of a growth hormone and the use of labor intensive procedures such as the clipping of flag leaves. The seeds formed on each parent are recovered in bulk and are separated on the basis of a genetic marker. The hybrid rice plants of the $F_1$ generation unlike those of the seed parent possess long flag leaves which extend upwardly to a greater maximum height than the tips of the panicles whereby photosynthesis can be accomplished on an efficient basis.

46 Claims, 4 Drawing Sheets

OTHER PUBLICATIONS

*Oryza Perennis*, by Hiko-Ichi Oka an Hiroko Morishima, *Evaluation*, vol. 21 pp. 249 to 258 (1967).

"Genetic Variability in Floral Characteristics Influencing Outcrossing in *Oryza sativa* L.", by S. S. Virmani and D. S. Athwal, *Crop Science*, vol. 13, pp. 66–67 (1973).

"Inheritance of Floral Characteristics Influencing Outcrossing in Rice", S. S. Virmani and D. S. Athwal, *Crop Science*, vol. 14, pp. 350–353 (1974).

"Variation in Components of Flowering Behaviour of Rice", by K. S. Parmar, E. A. Siddiq and M. S. Swaminathan, *Indian J. Genet.* vol. 39, pp. 542 to 550 (1979).

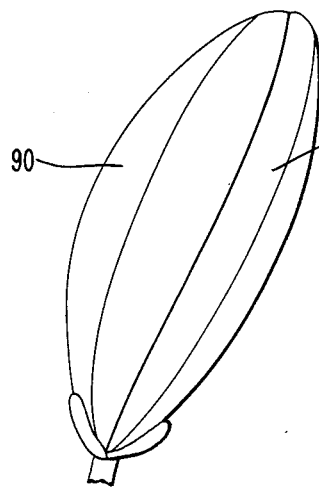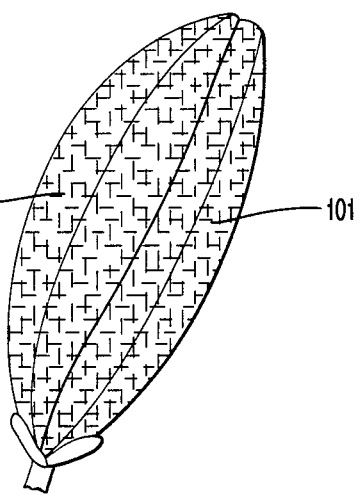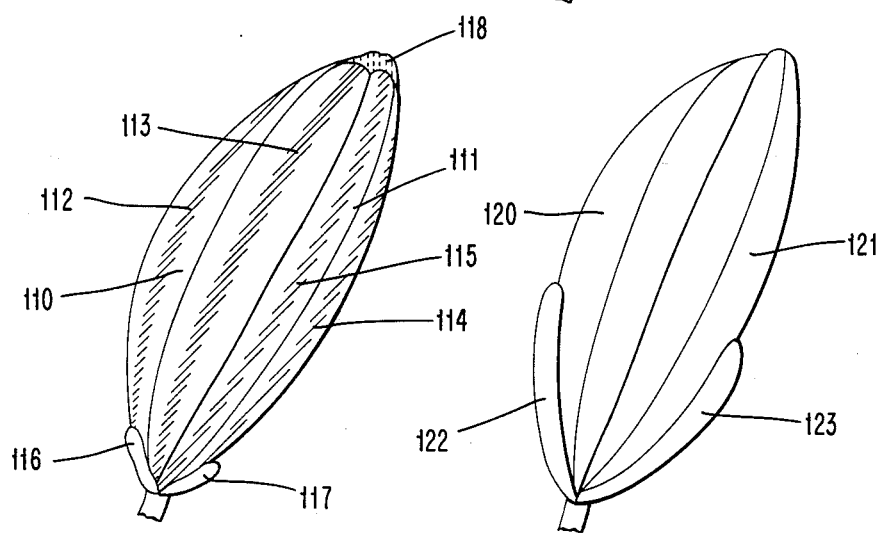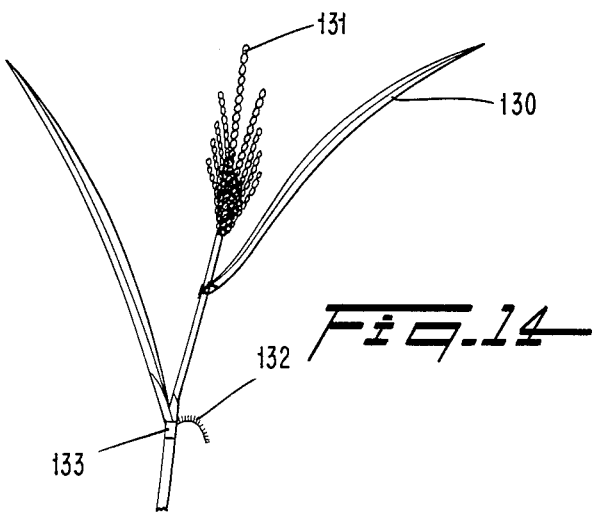

ROUTE TO HYBRID RICE PRODUCTION

BACKGROUND OF THE INVENTION

Rice (i.e., *Oryza sativa*) is recognized to be an important food crop in many parts of the world. However, heretofore rice production has not benefited to a substantial degree from heterosis or hybrid vigor made possible when different parental lines are cross-pollinated. For a number of reasons primarily related to the unique rice plant morphology, the controlled cross-pollination of rice plants has been difficult to achieve on a commercial scale.

Representative articles which discuss hybrid rice production are:
(1) "Hybrid Rice—Problems and Potentials", by J. W. Stansel and J. P. Craigmiles, Rice Journal, Vol 69, No. 5, Pages 14 to 15, and 46 (1966).
(2) "Outlook for Hybrid Rice in the USA", by H. L. Carnahan, J. R. Erikson, S. T. Tseng, and J. N. Rutger, Rice Breeding, International Rice Research Institute, Laguna, Philippines, Pages 603 to 607 (1972).
(3) "Outlook for Hybrid Rice in India", by M. S. Swaminathan, E. A. Siddig, and S. D. Sharma, Rice Breeding, International Rice Research Institute, Laguna, Philippines, Pages 609 to 613 (1972).
(4) "Current Status and Future Prospects for Breeding Hybrid Rice and Wheat", S. S. Virmani and Jan B. Edwards, *Advances in Agronomy*, Vol. 36, Pages 145 to 214 (1983).
(5) "A Concise Course in Hybrid Rice", by Long P. Yuan, Hunan Science and Technology Publishers, Hunan, China, Pages 1 to 168 (1985).
(6) "Current Status of Hybrid Rice Research and Development", by L. P. Yuan and S. S. Virmani, International Symposium on Hybrid Rice, Changsha, Hunan, China, Pages 1 to 16 plus tables (1986).

In U.S. Pat. No. 4,305,225 to Long P. Yuan, techniques are disclosed for aiding the production of hybrid rice. For instance, the male sterile seed parent plants can be sprayed with a growth hormone (e.g., gibberellin) in order to cause the flower-bearing panicles to more fully emerge from the rice leaf sheath. Any portion of the panicle which does not emerge will be incapable of receiving pollen from the pollen parent and thereby diminishes the yield of seeds capable of forming $F_1$ hybrid rice. The application of the growth hormone adds a significant expense to the overall process.

In U.S. Pat. No. 4,351,130 to J. Neil Rutger et al a rice hybridization process is disclosed wherein the male pollinator plants are recessively inherited tall plants.

In U.S. Pat. No. 3,842,538 to Zoltan Barabas is disclosed a hybrid seed production process wherein hybrid grains and pure grains are separated on the basis of color. Unlike wheat and similar grains, rice grains possess an outer hull which if removed will normally reduce their viability for planting purposes.

Heretofore, hybrid rice production has been carried out in the Peoples Republic of China using a highly labor intensive technique wherein the male and female rice parents are first seeded separately at different times in different beds, transplanted to different adjoining areas, monitored for growth on a weekly basis by observing the leaf count, the rate of growth is adjusted by water and fertilizer management, a growth hormone such as gibberellin is applied to the seed parent plants in order to cause the flower panicles to be more fully exserted out of the leaf sheath, the flag leaves of the seed parent plants are clipped, if wind currents are deficient pollen sometimes is transferred by hand through the movement of a rope across the planting area, and the seeds which are capable of forming $F_1$ hybrid rice plants are selectively harvested.

It is an object of the present invention to provide an improved procedure for forming seeds capable of growing male fertile $F_1$ hybrid rice plants which is capable of being readily implemented on a commercial scale.

It is an object of the present invention to provide an improved procedure for forming seeds capable of growing male fertile $F_1$ hybrid rice plants which can be carried out on a relatively economical basis without the need for extensive hand labor.

It is an object of the present invention to provide an improved procedure for forming seeds capable of growing male fertile $F_1$ hybrid rice plants which can be carried in the absence of the application of a growth hormone.

It is an object of the present invention to provide an improved procedure for forming seeds capable of growing male fertile $F_1$ hybrid rice plants which requires no clipping of flag leaves.

It is an object of the present invention to provide an improved procedure for forming seeds capable of growing male fertile $F_1$ hybrid rice plants wherein the parent plants optionally may be grown in a substantially random population.

It is an object of the present invention to provide an improved procedure for forming seeds capable of growing male fertile $F_1$ hybrid rice plants wherein in a preferred embodiment the parent plants are each provided with at least one distinctive vegetative marker which is useful to identify the presence and concentrations of the key plants.

It is an object of the present invention to provide an improved procedure for forming seeds capable of growing male fertile $F_1$ hybrid rice plants wherein the seeds formed on the parent plants may be simply harvested in bulk, and the seeds capable of growing male fertile $F_1$ hybrid rice plants subsequently substantially separated from the seeds formed on the male parent plants.

It is another object of the present invention to provide a substantially homogeneous assemblage of rice seeds which upon growth yields female fertile cytoplasmically male sterile rice plants possessing a combination of characteristics which renders them particularly suited for use as a seed parent for use in hybrid rice production.

It is a further object of the present invention to provide cytoplasmically male sterile rice plants which possess a combination of characteristics which renders them particularly suited for use as a seed parent in hybrid rice production.

These and other objects, as well as the scope, nature, and utilization of the claimed invention will be apparent to those skilled in the art from the following detailed description and appended claims.

SUMMARY OF THE INVENTION

It has been found that an improved process for the efficient production of seeds capable of growing male fertile $F_1$ hybrid *Oryza sativa* plants comprises:

(a) growing in a planting area a population of (i) female fertile cytoplasmically male sterile rice plants having substantially fully exserted stigmas, panicles which are substantially fully exserted in the absence of the application of growth hormone, flag leaves which in the absence of cutting generally extend upwardly to a lesser maximum height than the tips of the panicles whereby the panicles are well disposed to receive pollen from nearby plants and the disposition of the flag leaves below the tips of the panicles is attributable to recessive genes, and the ability to form seeds which are associated with a dominantly inherited genetic marker, and (ii) female fertile male fertile rice plants which are capable of restoring male fertility to the progeny of the cytoplasmically male sterile rice plants having generally long erect flag leaves attributable to dominant genes which generally extend upwardly to a greater maximum height than the tips of the panicles, and the ability to form seeds when self-pollinated which are associated with a recessively inherited genetic marker, (b) pollinating the population of rice plants whereby seeds are formed on the female fertile cytoplasmically male sterile rice plants (i) which are capable of growing male fertile $F_1$ hybrid rice plants having long flag leaves which generally extend upwardly to a greater maximum height than the tips of the panicles whereby efficient photosynthesis can be accomplished, and seeds are formed on the female fertile male fertile rice plants (ii) as a result of self-pollination, (c) recovering seeds which have formed on the rice plants growing in the planting area, and (d) substantially separating on the basis of the genetic marker the seeds capable of growing male fertile $F_1$ hybrid rice plants formed on the (i) plants from the seeds formed on the (ii) plants as a result of self-pollination.

An *Oryza sativa* seed product is provided consisting of a substantially homogeneous assemblage of seeds which upon growth yield female fertile cytoplasmically male sterile rice plants having substantially fully exserted stigmas, panicles which are substantially fully exserted in the absence of the application of growth hormone, flag leaves which in the absence of cutting generally extend upwardly to a lesser maximum height than the tips of the panicles whereby the panicles are well disposed to receive pollen from nearby plants and the disposition of the flag leaves below the tips of the panicles is attributable to recessive genes, and the ability to form seeds which are associated with a dominantly transmitted genetic marker.

Plants of *Oryza sativa* are provided which exhibit cytoplasmic male sterility, substantially fully exserted stigmas, panicles which are substantially fully exserted in the absence of the application of growth hormone, flag leaves which in the absence of cutting generally extend upwardly to a lesser maximum height than the tips of the panicles whereby the panicles are well disposed to receive pollen from nearby plants and the disposition of the flag leaves below the tips of the panicles is attributable to recessive genes, and the ability to form seeds which are associated with a dominantly transmitted genetic marker.

BRIEF DESCRIPTION OF THE DRAWINGS

FIG. 10 shows an enlarged schematic presentation of a preferred rice grain with hull capable of growing the male fertile $F_1$ hybrid rice plants which may be formed in accordance with the process of the present invention. The hull consisting of the lemma 90 and palea 91 is a straw-colored as the result of a dominantly inherited trait.

FIG. 11 shows an enlarged schematic presentation of a preferred rice grain with hull which may result from the self-pollination of a female fertile male fertile restorer rice plant during the course of the process of the present invention. The hull consisting of lemma 100 and palea 101 is gold-colored as the result of a recessively inherited trait. The gold-colored hull of FIG. 11 can readily be separated from the straw-colored hull of FIG. 10 through the use of photoelectric seed-sorting equipment.

FIG. 12 shows an enlarged schematic presentation of a preferred rice grain with hull which may be formed in accordance with the process of the present invention. The hull consisting of lemma 110 and palea 111 possesses distinctive dark-brown longitudinal furrows 112, 113, 114, and 115, rudimentary glumes 116 and 117, and a purple-colored apiculus 118. Each of these characteristics is dominantly inherited and can be present individually or in combinations of two or more. Such characteristics alone or in combination can be used as a basis for seed separation in the process of the present invention.

FIG. 13 shows an enlarged schematic presentation of a preferred rice grain with hull which may result from the self-pollination of a female fertile male fertile restorer rice plant during the course of the process of the present invention. The hull consisting of lemma 120 and palea 121 is relatively smooth and lacks dark-brown longitudinal furrows. Large empty glumes 122 and 123 are present, and a purple-colored apiculus is absent. Each of these characteristics is recessively inherited and can be encountered individually or in combinations of two or more. Such characteristics alone or in combination can be used as a basis for seed separation in the process of the present invention.

FIG. 14 shows a representative portion of a male fertile $F_1$ hybrid rice plant resulting from seed formed in accordance with the process of the present invention. Unlike the seed parent plants of FIGS. 3, 4, 5 and 6, the flag leaf 130 at the time of flowering extends upwardly to a greater maximum height than the tip of the panicle 131 whereby efficient photosynthesis can be accomplished. It will be noted, however, that the flag leaf 130 of the $F_1$ hybrid rice plant commonly will extend upwardly to a lesser extent than the flag leaf 70 of the female fertile male fertile restorer rice plant of FIG. 8 because the dominantly inherited trait for flag leaf disposition commonly is only partially expressed in the $F_1$ generation. In a preferred embodiment a vegetative marker in the form of a substantially purple-colored auricle 132 a substantially purple-colored collar 133 also is present.

DETAILED DESCRIPTION OF PREFERRED EMBODIMENTS

The cytoplasmic-genetic system for hybrid rice production is well known to those skilled in rice technology and presently is being carried out in the Peoples Republic of China on a large scale. There the desired heterosis or hybrid vigor is being achieved; however, the hybridization technique there practiced is highly labor intensive and accordingly is unsuited for implementation in those parts of the world where labor costs are relatively more costly.

In accordance with the concept of the present invention the phenotypes of the cytoplasmically male sterile seed parent rice plants and the maintainer rice plants for the same initially are modified (as described) so as to overcome significant hybridization obstacles found to be inherently associated with the corresponding rice plants of the prior art. The rice plants may be of either the indica or japonica types. Rice plants of the japonica type commonly are grown in cooler regions. The modification can be carried out by conventional plant breeding techniques, or other more recently available plant modification procedures, such as tissue culture (somaclonal, cell, anther), genetic engineering, protoplast fusion, etc.

Preferred cytoplasms for the cytoplasmically male sterile plants of the present invention may be derived from a sporophytic system using an indica source, such as WA (wild abortive), Gam (Gambiaca), DW (dwarf wild rice with aborted pollen), ARC (IRRI line), L (lead rice), etc., or from a gametophytic system from a japonica source, such a BT (Chinsurah Borro II), etc. Other cytoplasmically male sterile cytoplasms alternatively may be selected.

Figure 1:
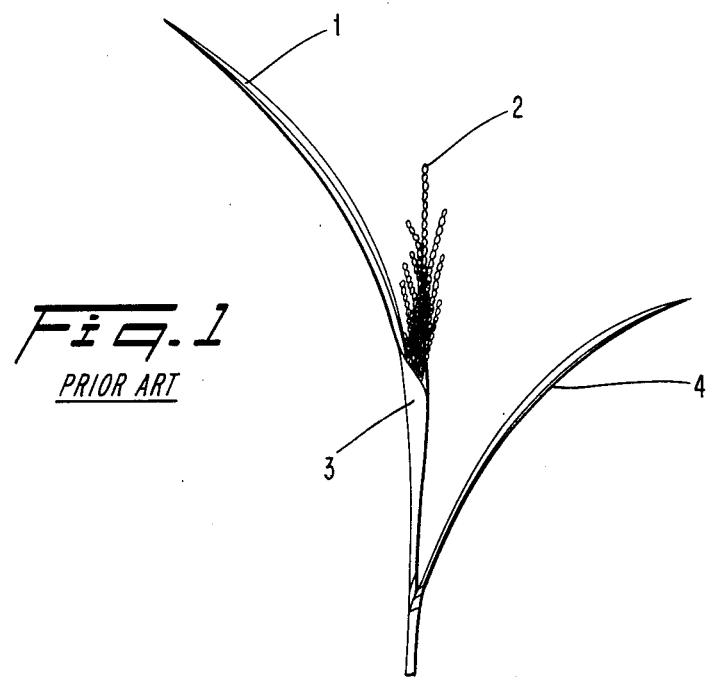
FIG. 1 shows a portion of a representative cytoplasmically male sterile rice plant of the indica type of the prior art wherein the flag leaf 1 at the time of flowering in the absence of cutting extends upwardly to a greater maximum height than the tip of floral panicle 2, and approximately 10 to 25 percent or more of the panicle is non-exserted and is enclosed by leaf sheath 3. The leaf 4 below the flag leaf 1 is also erect. In accordance with the prior art such flag leaf 1 commonly is cut either by hand or by a hand-held mechanized cutter.

Indica cytoplasmically male sterile rice plants heretofore available have possessed the undesirable trait as illustrated in FIG. 1 of having a portion of the floral panicle inserted within the leaf sheath. The japonica cytoplasmically male sterile rice plants do not possess this undesirable trait. Accordingly, the florets present upon the inserted portion of the panicle of the indica rice plants are never provided access to the pollen required to achieve cross-pollination and the yield of seed capable of forming $F_1$ hybrid rice plants accordingly is diminished. In order to deal with this deficiency a growth hormone such as gibberellin sometimes has been applied in the prior art in order to cause increased peduncle growth and the full exsertion of the floral panicle. Such growth hormone is expensive, requires additional equipment and labor to apply, its application must be coordinated with the absence of rainfall, etc.

In accordance with the concept of the present invention cytoplasmically male sterile rice plants are provided (e.g., as illustrated in FIGS. 3, 4, 5 and 6) which possess panicles which at the time of flowering are substantially fully exserted from the leaf sheath in the absence of the application of a growth hormone in combination with the other characteristics recited herein. Accordingly, the florets along the full length of the panicles have access to pollen and the costly application of a growth hormone is not required to achieve such access. The achievement of such substantially full panicle exsertion in the cytoplasmically male sterile plants of the indica type can be produced by the introduction of such trait from an appropriate source such as pureline selections from the crosses Belle Patna/Zenith//Belle Patna/MOR 500, Saturn, Zenith, AS2004, the eui eui germplasm (elongated upper internode-genetic tall recessive line 80-14549 available from J. Neil Rutger of Davis, California), etc.

Figure 2:
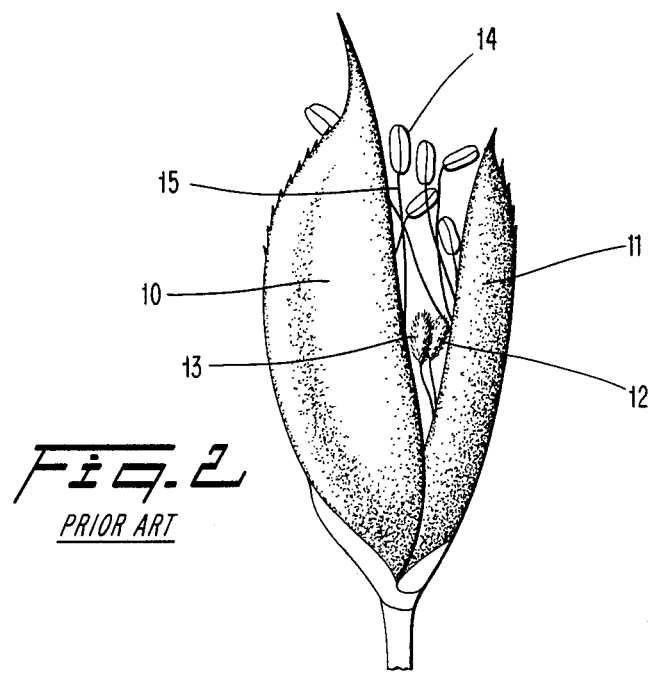
FIG. 2 shows an enlarged schematic presentation of a representative open floret from the floral panicle of the cytoplasmically male sterile rice plant of the prior art as shown in FIG. 1. The lemma 10 and palea 11 open only once to a maximum angle of only approximately 10 to 25 degrees, and the pair of stigmas 12 and 13 borne on relatively short styles is nonexserted and is enclosed when the lemma 10 and palea 11 are permanently returned to their unopened positions. A representative stamen is composed of an anther 14 and a filament 15. No viable pollen is produced.

Cytoplasmically male sterile rice plants heretofore reported have tended to display the usual rice stigma disposition as illustrated in FIG. 2. More specifically, the stigmas have tended to be situated well within the glume (i.e., the lemma and palea) of a given floret and to be available for receipt of pollen only for a relatively brief period of time (e.g., approximately 30 to 120 minutes) when the floret is open. Also, as illustrated in FIG. 2, during flowering the lemma and palea of the floret commonly open to an angle of only approximately 10 to 25 degrees.

Figure 7:
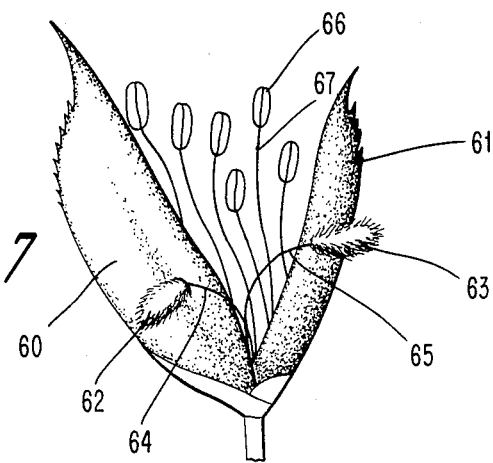
FIG. 7 shows an enlarged schematic presentation of a representative open floret from the floral panicle of the cytoplasmically male sterile rice plants of FIGS. 3, 4, 5 and 6 of the present invention. The lemma 60 and palea 61 open to a maximum angle of approximately 45 degrees; however, the angle of opening optionally may be lesser so long as the stigmas 62 and 63 which are borne on relatively long styles 64 and 65 are substantially fully exserted and remain substantially exposed even when the lemma 60 and palea 61 are permanently returned to their unopened position. The exact number of stigmas per floret may vary. A representative stamen is composed of an anther 66 and a filament 67. No viable pollen is produced.

In accordance with the concept of the present invention cytoplasmically male sterile rice plants are provided (e.g., as illustrated in FIG. 7) which possess stigmas at the time of flowering which are substantially fully exserted. Such stigmas remain substantially exposed even after the lemma and palea close thereby substantially extending the period of time from up to 2 hours to approximately 4 to 5 days during which pollination may occur. Such stigma exsertion may be attributable to the length of the styles on which the stigmas are borne and/or the stigma length. Also, in a preferred embodiment as illustrated in FIG. 7 the lemma and palea open to a greater angle than normally encountered in rice florets which further aids in the disposition of the stigmas outside the lemma and palea. In a particularly preferred embodiment the lemma and palea open to an angle of approximately 30 to 45 degrees. Also, in a preferred embodiment cytoplasmically male sterile rice plants optionally may be selected which possess more than the usual number of two stigmas per floret and accordingly exhibit three to five stigmas, or more per floret. The achievement of such substantially full stigma exsertion in the cytoplasmically male sterile plants can be produced by crossing an exserted stigma source such as *Oryza rufipogon* and/or *Oryza longistaminata* to Oryza sativa, making selections for 5 or 6 generations, crossing to a variety with good agronomic characteristics, making selections for 5 or 6 generations, crossing to a cytoplasmically male sterile line, making 5 or 6 backcrosses, and making a selection for a cytoplasmically male sterile plants having the desired substantially fully exserted stigmas. In the past such exserted stigma characteristic generally has not been reported in *Oryza sativa* plants of the japonica type. Mulipistillate rice plants can be derived from japonica cultivar wx 154 available from Yeungan University of Gyeongsa, Korea, etc.

Heretofore, the cytoplasmically male sterile rice plants utilized in hybrid rice production if left unaltered (as illustrated in FIG. 1) commonly have possessed a flag leaf which extends upwardly to greater maximum height than the tip of the floral panicle. Such flag leaf configuration is genetically controlled and has proven to pose a partial barrier to the receipt of pollen required for cross-pollination. In the rice hybridization process previously practiced the upper portions of such flag leaves commonly are laboriously removed by cutting so as to remove this impediment to cross-pollination. Such cutting is highly time consuming, very expensive, and difficult to achieve with accuracy in the absence of concomitant damage to the floral panicles. Known varieties of cytoplasmically male sterile rice plants can be modified so as to incorporate atypical flag leaves which at the time of flowering in the absence of cutting generally extend upwardly to a lesser maximum height than the tips of the panicles. Such lower disposition of the flag leaves is attributable to recessive genes. The disposition of the leaves below the flag leaf commonly is independent of the flag leaf disposition and is separately controlled. In a preferred embodiment, the leaves below the flag leaf are erect. Also, in a preferred embodiment at least 50 percent of the total panicle height at the time of flowering generally extends above the maximum height of the flag leaves of the female fertile cytoplasmically male sterile rice plants. A high level of cross-pollination is made possible in the absence of any substantial obstruction posed by flag leaves.

Figure 3:
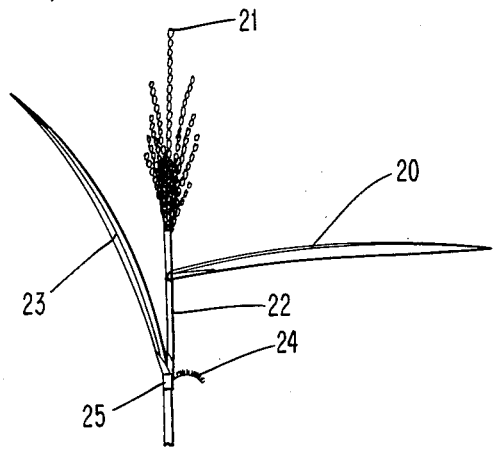
FIG. 3 shows a portion of a representative cytoplasmically male sterile rice plant suitable for use in the present invention wherein the flag leaf 20 at the time of flowering is disposed in a substantially horizontal configuration which is attributable to recessive genes. The flag leaf 20 at the time of flowering extends upwardly to a lesser maximum height than the tip of the floral panicle 21. Also, the panicle 21 is substantially fully exserted from the leaf sheath 22 in the absence of the application of a growth hormone. The leaf 23 below flag leaf 20 is erect; however, it optionally may assume a different configuration. In a preferred embodiment a vegetative marker in the form of a substantially white auricle 24 and a substantially white collar 25 also is present.

In a preferred embodiment of the present invention, the female fertile cytoplasmically male sterile rice plants at the time of flowering possess flag leaves which are disposed in a substantially horizontal configuration as illustrated in FIG. 3 which is attributable to recessive genes. The substantially horizontal flag leaf character can be introduced into the cytoplasmically male sterile seed parent plants by crossing with Bonnet Bell, pureline selections from Labelle/Melrose, etc.

Figure 4:
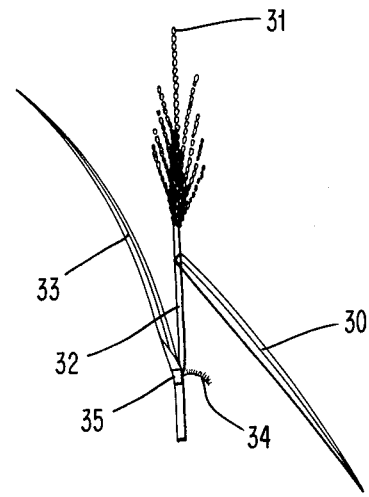
FIG. 4 shows a portion of another representative cytoplasmically male sterile rice plant suitable for use in the present invention wherein the flag leaf 30 at the time of flowering is disposed in an decumbent configuration which is attributable to recessive genes. The flag leaf 30 at the time of flowering extends upwardly to a lesser maximum height than the tip of the floral panicle 31. Also, the panicle 31 is substantially fully exserted from the leaf sheath 32 in the absence of the application of a growth hormone. The leaf 33 below the flag leaf 30 is erect; however, it optionally may assume a different configuration. In a preferred embodiment a vegetative marker in the form of a substantially white auricle 34 and a substantially white collar 35 also is present.

In another preferred embodiment of the present invention the female fertile cytoplasmically male sterile rice plants at the time of flowering possess flag leaves which are disposed in a decumbent configuration (i.e., are generally borne at an angle with respect to the rice stalk of no more than approximately 80 degrees) as illustrated in FIG. 4 which is attributable to recessive genes. Commonly such decumbent flag leaves are borne at an angle of approximately 40 to 80 degrees with respect to the rice stalk. The decumbent flag leaf character can be introduced into the cytoplasmically male sterile seed parent plants by crossing with Labelle, selections from CI9157/G630, etc.

Figure 5:
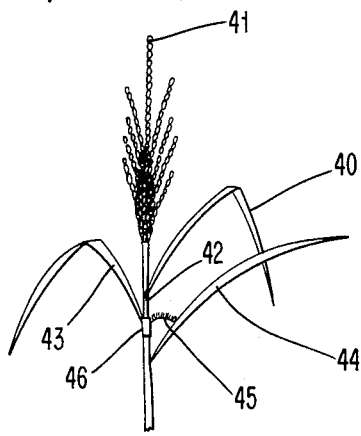
FIG. 5 shows a portion of another representative cytoplasmically male sterile rice plant suitable for use in the present invention wherein the flag leaf 40 at the time of flowering is disposed in a downwardly arching configuration which is attributable to recessive genes. The flag leaf 40 at the time of flowering extends upwardly to a lesser maximum height than the tip of the floral panicle 41. Also, the panicle 41 is substantially fully exserted from the leaf sheath 42 in the absence of the application of a growth hormone. The configurations of leaves 43 and 44 below the flag leaf 40 may be varied without departing from the concept of the present invention. In a preferred embodiment a vegetative marker in the form of a substantially white auricle 45 and a substantially white collar 46 also is present.

In another embodiment of the present invention, the female fertile cytoplasmically male sterile rice plants at the time of flowering possess flag leaves which are disposed in a downwardly arching configuration as illustrated in FIG. 5 which is attributable to recessive genes. The downwardly arching flag leaf character can be introduced into the cytoplasmically male sterile seed parent plants by crossing with Lebonnet, Brazos, etc.

Figure 6:
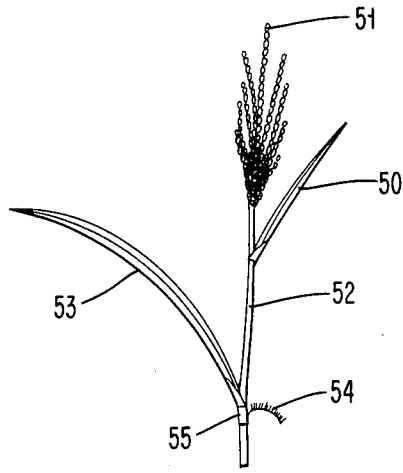
FIG. 6 shows a portion of another representative cytoplasmically male sterile rice plant suitable for use in the present invention wherein the flag leaf 50 at the time of flowering is short and substantially erect with such configuration being attributable to recessive genes. The flag leaf 50 at the time of flowering extends upwardly to a lesser maximum height than the tip of the panicle 51. Also, the floral panicle 51 is substantially fully exserted from the leaf sheath 52 in the absence of the application of a growth hormone. The configuration of leaf 53 below flag leaf 50 is erect; however, it optionally may assume a different configuration. In a preferred embodiment a vegetative marker in the form of a substantially white auricle 54 and a substantially white collar 55 also is present.

In yet another embodiment of the present invention, the female fertile cytoplasmically male sterile rice plants at the time of flowering possess flag leaves which are disposed in a short substantially erect configuration as illustrated in FIG. 6 which is attributable to recessive genes. The short erect flag leaf character can be introduced into the cytoplasmically male sterile seed parent plants by crossing with Brachytic Nato, selections from Brachytic Nato/C57, etc.

Finally, it is essential that the cytoplasmically male sterile plants of the present invention possess the ability to form seeds which are associated with a dominantly inherited genetic marker. Such marker is either on or about the rice hull. As described hereafter, such genetic marker will enable the separation of seeds capable of growing male fertile $F_1$ hybrid rice plants formed thereon from seeds formed on the male parent restorer plants as the result of self-pollination. Markers on the rice seeds per se are ineffective for use in the present invention since the rice seeds are located within a protective hull. If such hull is removed to expose the seed, the capability of the rice seed to produce a rice plant is greatly reduced.

In a preferred embodiment such dominantly transmitted genetic marker which is associated with the seeds is a straw-colored hull as illustrated in FIG. 10. The straw-colored hull characteristic is common in rice plants and can be introduced into the male sterile seed parent plants by crossing with Labelle, Lebonnet, Newrex, Della, Starbonnet, Bonnet 73, Lemont, Bellemont, Nato, Vista, Saturn, Brazos, Nova 76, Mars, etc.

In other embodiments the dominantly transmitted genetic marker which is associated with the seeds as illustrated in FIG. 12 consists of distinctive dark-brown longitudinal furrows 112, 113, 114, and 115 on the lemma and palea 110 and 111, rudimentary glumes 116 and 117, a purple-colored apiculus 118, or combinations of two or more of these. The dark-brown longitudinal furrow characteristic can be introduced into the cytoplasmically male sterile seed parent plants by crossing with Ikam Podchee. The rudimentary glumes optionally can possess a distinctive coloration and can be introduced into the cytoplasmically male sterile seed parent plants by crossing with Nortai, PI408449, CI5309, purple Starbonnet, etc. The purple-colored apiculus can be introduced into the cytoplasmically male sterile seed parent plants by crossing with Nortai, Bonnet 73, PI408449, etc.

Additional representative dominantly transmitted markers which optionally can be associated with the seeds of the cytoplasmically male sterile plants of the present invention include purple-colored hulls, rough-/pubescent hull surfaces, and depressed palea. The rough/pubescent hull surfaces can be introduced into the cytoplasmically male sterile seed parent plants by crossing with Calrose 76, Earlirose, Colusa, Caloro, Yong Kwang, etc. The depressed palea can be introduced into the cytoplasmically male sterile seed parent plants by crossing with ECCA-90.

The cytoplasmically male sterile rice plants of the present invention preferably also possess at least one additional marker which manifests itself in the vegetation so that the female parent plants readily can be distinguished from the male fertile restorer plants. Such marker enables one readily to confirm the presence of the cytoplasmically male sterile plants and further provides a means to determine the approximate concentration of the same in a given rice plant population. Accordingly, such markers provide those who produce seeds capable of growing male fertile $F_1$ hybrid rice plants with a means to well monitor the required seed parent plants prior to and during utilization in the process of the present invention. Corrective action can be taken at an early stage in the hybrid seed production process should this be required. Unwanted plants can be rogued from the area if a certain marker or combination of markers is absent.

A preferred vegetative marker for use with the cytoplasmically male sterile plants of the present invention is a light (e.g., white, off-white, light-green, yellow, tan) auricle and collar. Such auricles are small hairy-like appendages which tend to be sickle-shaped situated adjacent the leaf collar at the junction of the leaf sheath and the leaf blade. The auricles and leaf collars are illustrated adjacent a single leaf in FIGS. 3, 4, 5, and 6; however, in practice such auricles and collars commonly will recur a number of times in each rice plant in conjunction with each leaf. In a particularly preferred embodiment the light auricle and collar is substantially white and is common to most rice varieties. Alternatively, dark (e.g., purple, red, etc.) auricles and collars may be selected in less preferred embodiments. Such purple auricles and collars can be derived from Arborio, and selections from the cross of A8/-/VEC/G630. Recessively transmitted green leaf sheaths, green peduncles, and/or green leaf margins or dominantly transmitted purple leaf sheaths purple peduncles, and/or purple leaf margins may be selected. Green leaf sheaths, green peduncles, and/or green leaf sheaths are common in many rice varieties. The purple leaf sheaths, peduncles, and margins may be derived from PI408449, CI5309, the cross of Labelle/Melrose//G630, etc. Stigma color (e.g. dark stigmas such as purple or red stigmas vs. white stigmas) may be utilized as a vegetative marker. Purple stigmas can be derived from Nortai, V41A, V20A, Bonnet 73, CI5309, purple Starbonnet, PI408449, etc. Red stigmas can be derived from Lemont, Leah, etc. White stigmas can be derived from Phi-Gai, Newrex, IR24, R29, etc. Also, the presence or absence of leaf pubescence can be used as a vegetative marker.

Figure 8:
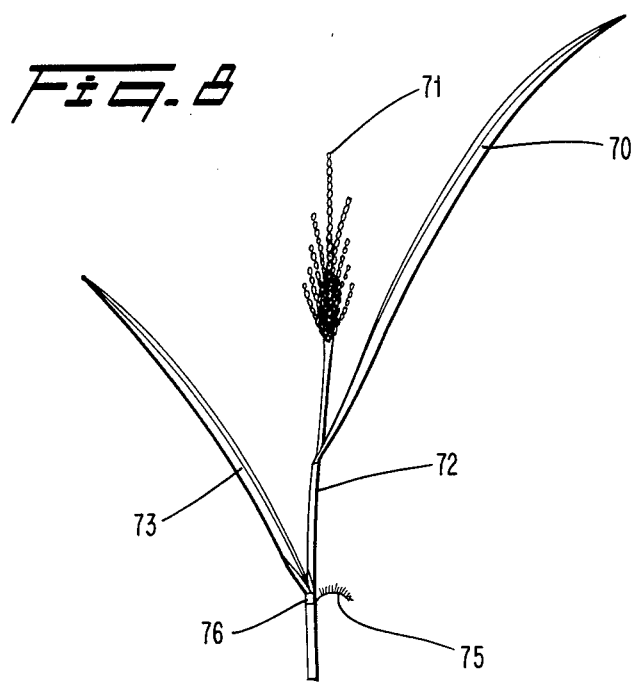
FIG. 8 shows a portion of a representative female fertile male fertile restorer rice plant which is suitable for use in the process of the present invention. The flag leaf 70 at the time of flowering is long and erect and extends upwardly to a greater maximum height than the tip of the floral panicle 71. The configuration of the flag leaf 70 at the time of flowering is attributable to dominant genes. The floral panicle 71 is substantially fully exserted from the leaf sheath 72 in the absence of the application of a growth hormone; however, it is not essential that the floral panicle be substantially fully exserted as illustrated. The configuration of leaf 73 below the flag leaf 70 also is erect; however, it optionally may assume a different configuration. In a preferred embodiment a vegetative marker in the form of substantially purple-colored auricle 75 and a substantially purple-colored collar 76 also is present.

When carrying out the process of the present invention, female fertile male fertile rice plants are employed which are capable of restoring male fertility to the progeny of the cytoplasmically male sterile rice plants and possess the other required characteristics recited herein. As illustrated in FIG. 8, such male parent restorer plants have generally long erect flag leaves attributable to dominant genes which generally extend upwardly to a greater maximum height that the tips of the panicles.

Such male parents may be derived from known rice varieties which have been modified by plant breeding or other means to incorporate the recessively inherited genetic marker associated with the seed as described hereafter. Representative commercially available rice varieties which exhibit dominantly inherited long erect flag leaves include Lemont, Bluebelle, Bonnet 73, Bellemont, IR24, IR36, IR54, G630, selections from the cross of IR24/Yuang Hsing, selections from the cross of LM/G630, etc.

The restorer rice plants possess the same genetic marker associated with the seeds as is present in the cytoplasmically male sterile seed parent rice plants with the exception that the marker is present in the homozygous recessive form in the restorer plants and is present in the homozygous dominant form in the seed parent plants. For instance, if the seed parent possesses a straw-colored hull as illustrated in FIG. 10, the restorer plants can possess a gold-colored hull as illustrated in FIG. 11. Such gold-colored hull can be introduced into the restorer plants by crossing a variety having a gold-colored hull with a restorer variety having a straw-colored hull, selecting plants having a gold-colored hull in the $F_2$ generation, backcrossing 4 to 6 times, and making the final selection. Rice plants having a gold-colored hull can be derived from Bluebelle, Dawn, gold Nato, Kar 398, Dular gold, Pecos, Kargat 184, etc. If the seed parent possess rudimentary glumes as illustrated in FIG. 12, the restorer plants can possess the long empty glumes as illustrated in FIG. 13 or rudimentary glumes of a different color. The presence of long empty glumes in the restorer plants can be derived from 83N1223 available from the Crowley Rice Experiment Station, Crowley, LA, U.S.A. If the seed parent possesses a purple-colored apiculus, the restorer plants can possess a substantially white apiculus. Such white apiculus can be introduced into the restorer plants by crossing with Lebonnet, Bellemont, Newrex, Starbonnet, Brazos, Saturn, Mars, etc. If the seed parent possesses dark-brown longitudinal furrows on the hull, the restorer plants can possess a hull which lacks such dark-brown coloration, such as a straw-colored hull. Such absence of dark-brown hull coloration in the restorer plants is readily available in many rice varieties.

In a preferred embodiment the female fertile male fertile rice plants which serve as restorers also possess at least one additional marker which manifests itself in the vegetation so that the restorer plants readily can be distinguished from the cytoplasmically male sterile plants. In each instance the restorer rice plants possess the same vegetative marker or markers as present in the cytoplasmically male sterile seed parent plants with the exception that such marker or markers are present in the reciprocal state (i.e., if present in the seed parent in a homozygous dominant form, are present in the restorer parent in the homozygous recessive form, or if present in the seed parent in a homozygous recessive form, are present in the restorer parent in the homozygous dominant form). For instance, in a preferred embodiment as illustrated in FIG. 8 the restorer plants will exhibit purple-colored auricles and purple-colored collars which are dominantly transmitted. An auricle and collar is illustrated adjacent a single leaf in FIG. 8; however, in practice the auricles and collars will recur a number of times in each rice plant in conjunction with each leaf.

Figure 9:
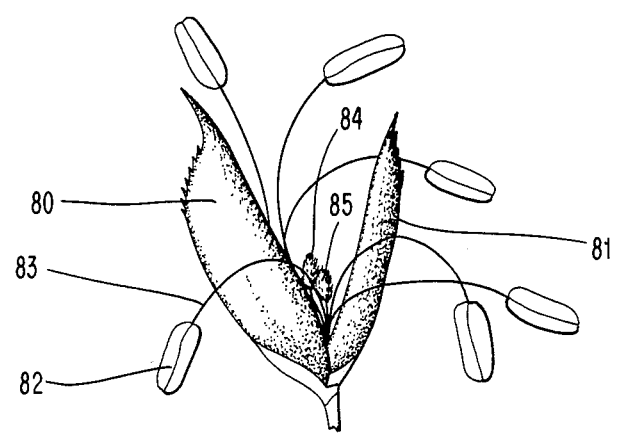
FIG. 9 shows an enlarged schematic presentation of a representative open floret from the floral panicle of a preferred female fertile male fertile restorer rice plant of FIG. 8 which is particularly suited for use in the process of the present invention. The lemma 80 and palea 81 open to an angle of approximately 30 to 45 degrees; however, the angle of opening optionally may be lesser. A representative stamen is composed of an anther 82 and a filament 83. The anthers preferably are extruded so that they remain outside even when the lemma 80 and palea 81 are permanently returned to their unopened position. The anthers will disperse viable pollen which preferably has a relatively long fertility duration. The disposition of stigmas 84 and 85 is not important to the operation of the process of the present invention.

As illustrated in FIG. 9, the female fertile male fertile restorer rice plants in a preferred embodiment additionally possess fully extruded anthers which are well able to disperse pollen. Such anthers are extruded in the sense that they protrude outside when the lemma and palea open. Such extruded anther characteristic can be introduced into the restorer plants by crossing with *Oryza longistaminata* and/or *Oryza rufipogon* followed by backcrossing and selection. It is preferred that the stigmas of the restorer plants be non-exserted so as to minimize the possibility of out-crossing. It also is preferred that the pollen be formed on the restorer plants over an extended period of time in abundant quantities and that it be light and buoyant to facilitate easy dispersion. Such pollen dispersion also is aided if the restorer plants are generally equal or greater in height than the seed parent plants. It is also preferred that the restorer plants produce pollen of relatively long fertility duration.

The parent plants for use in the process of the present invention are selected so that at least a general synchronization of flowering occurs. Thereby, pollen from the restorer plants is present when the florets of the seed parent plants are receptive to pollination. If one of the parents tends to mature more rapidly than the other, the more rapidly maturing parent may be planted at a later date or its seeds may be coated prior to planting to retard germination. Alternatively, mixtures of soaked and unsoaked seeds may be planted in order to prolong the time in which pollen is dispersed. Also, it is preferable that the parent plants possess relatively smooth leaf surfaces which are substantially incapable of retaining the pollen which contacts the same. Accordingly, the pollen released by the restorer plants has a greater potential to reach florets of the seed parent plants.

In accordance with a preferred embodiment of the present invention the parent plants are grown in a planting area in a substantially random population. Alternatively, in a less preferred embodiment the parent plants are grown as adjacent substantially homogeneous populations within the planting area. Such plants may be grown from seed in the planting area or transplanted as small immature plants into the planting area Commonly, approximately 70 to 80 percent of the plants in the planting area are cytoplasmically male sterile plants, and approximately 20 to 30 percent of the plants in the planting area are restorer plants. When the parent plants are grown as a substantially random population, the proportion of cytoplasmically male sterile plants can be maximized. For instance, in a random population in a particularly preferred embodiment approximately 85 to 95 percent of the rice plants can be cytoplasmically male sterile plants and approximately 5 to 15 percent (e.g., 10 percent) of the rice plants can be the restorer plants.

During the course of the process of the present invention the cytoplasmically male sterile plants are pollinated with pollen from the restorer plants and the restorer plants are self-pollinated. The pollen transfer between the restorer plants and the cytoplasmically male sterile plants commonly is carried out by wind transport. However, other means capable of moving the pollen alternatively can be selected.

At the appropriate time in the life cycle of the parent plants the rice seeds formed on the parent plants are recovered in bulk. Such harvesting can efficiently be carried out through the use of a conventional rice combine.

Next, the seeds capable of growing male fertile $F_1$ hybrid rice plants formed on the cytoplasmically male sterile rice plants are separated from the seeds formed on the restorer plants on the basis of the genetic marker which is associated with the seeds. Such separation preferably is mechanized. For instance, photoelectric seed-sorting equipment, velvet rolls, mechanical seed sorters which respond to seed size and/or shape, etc. can be utilized. In a preferred embodiment the seeds capable of forming $F_1$ hybrid rice plants possess a straw-colored hull and the seeds formed on the restorer plants possess a gold-colored hull. The seeds having a gold-colored hull readily can be removed with ease at a high rate of speed using a photoelectric seed-sorting apparatus available from ESM International Inc., 9800 Townpark Rd., Houston, TS. 77036, U.S.A. The seeds possessing the straw-colored hull can be sold to those wishing to obtain the additional yields made possible through hybrid vigor. The seeds bearing a gold-colored hull which were produced on the restorer plants can be sold for conventional rice usages or retained for planting as a restorer in another generation.

As illustrated in FIG. 14, a representative male fertile $F_1$ hybrid rice plant made possible by the process of the present invention unlike the seed parent plants possesses a flag leaf which extends upwardly to a greater maximum height than the tip of the floral panicle. Accordingly, efficient photosynthesis is promoted in the $F_1$ generation in order to further maximize rice yields.

In a preferred embodiment of the process of the present invention the purity of the desired seed product is monitored through a determination of whether the seeds used to form plants (i) of step (a) inadvertently had become contaminated with seeds which were formed on nearby maintainer plants during the formation of the planting seed used in step (a) to form plants (i). This conveniently may be done by providing the seed parent plants (i) with recessively transmitted light (e.g., substantially white) auricles and collars, and providing the restorer plants (ii) with dark (e.g., substantially purple-colored) auricles and collars, growing at least a portion of the seeds (i.e., a representative sample) which are intended to form male fertile $F_1$ hybrid rice plants separated in step (d), and determining the approximate proportion of seeds capable of forming male fertile $F_1$ hybrid rice plants present therein having dark auricles and collars in comparison to undesired seeds which form plants having light auricles and collars resulting from the contained self-pollination of maintainer plants. Accordingly, the seed formed in accordance with the process of the present invention for the formation of $F_1$ hybrid rice plants can be accurately labeled as to its purity.

Although the invention has been described with preferred embodiments, it is to be understood that variations and modification may be resorted to as will be apparent to those skilled in the art. Such variations and modifications are to be considered within the purview and scope of the claims appended hereto.

I claim:

1. An improved process for the efficient production of seeds capable of growing male fertile $F_1$ hybrid *Oryza sativa* plants comprising:
    (a) growing in a planting area a population of (i) female fertile cytoplasmically male sterile rice plants having substantially fully exserted stigmas, panicles which are substantially fully exserted in the absence of the application of growth hormone, flag leaves which in the absence of cutting generally extend upwardly to a lesser maximum height than the tips of said panicles whereby said panicles are well disposed to receive pollen from nearby plants and the disposition of said flag leaves below the tips of said panicles is attributable to recessive genes, and the ability to form seeds which are associated with a dominantly inherited genetic marker, and (ii) female fertile male fertile rice plants which are capable of restoring male fertility to the progeny of said cytoplasmically male sterile rice plants having generally long erect flag leaves attributable to dominant genes which generally extend upwardly to a greater maximum height than the tips of the panicles, and the ability to form seeds when self-pollinated which are associated with a recessively inherited genetic marker,
    (b) pollinating said population of rice plants whereby seeds are formed on said female fertile cytoplasmically male sterile rice plants (i) which are capable of growing male fertile $F_1$ hybrid rice plants having long flag leaves which generally extend upwardly to a greater maximum height than the tips of the panicles whereby efficient photosynthesis can be accomplished, and seeds are formed on said female fertile male fertile rice plants (ii) as a result of self-pollination,
    (c) recovering seeds which have formed on said rice plants growing in said planting area, and
    (d) substantially separating on the basis of said genetic marker the seeds capable of growing male fertile $F_1$ hybrid rice plants formed on said (i) plants from the seeds formed on said (ii) plants as a result of self-pollination.

2. An improved process for the efficient production of seeds capable of growing male fertile $F_1$ hybrid *Oryza sativa* plants according to claim 1 wherein in step (a) said populations (i) and (ii) are grown in a substantially random population.

3. An improved process for the efficient production of seeds capable of growing male fertile $F_1$ hybrid *Oryza sativa* plants according to claim 1 wherein said rice plants are of the indica type.

4. An improved process for the efficient production of seeds capable of growing male fertile $F_1$ hybrid *Oryza sativa* plants according to claim 3 wherein the cytoplasm of said female fertile cytoplasmically male sterile rice plants (i) was derived from the WA cytoplasm.

5. An improved process for the efficient production of seeds capable of growing male fertile $F_1$ hybrid *Oryza sativa* plants according to claim 3 wherein the cytoplasm of said female fertile cytoplasmically male sterile plants (i) was derived from the Gam cytoplasm.

6. An improved process for the efficient production of seeds capable of growing male fertile $F_1$ hybrid *Oryza sativa* plants according to claim 3 wherein the cytoplasm of said female fertile cytoplasmically male sterile plants (i) was derived from the DW cytoplasm.

7. An improved process for the efficient production of seeds capable of growing male fertile $F_1$ hybrid *Oryza sativa* plants according to claim 3 wherein the cytoplasm of said female fertile cytoplasmically male sterile plants (i) was derived from the L cytoplasm.

8. An improved process for the efficient production of seeds capable of growing male fertile $F_1$ hybrid *Oryza sativa* plants according to claim 1 wherein said rice plants are of the japonica type.

9. An improved process for the efficient production of seeds capable of growing male fertile $F_1$ hybrid *Oryza sativa* plants according to claim 8 wherein the cytoplasm of said female fertile cytoplasmically male sterile plants (i) was derived from the BT cytoplasm.

10. An improved process for the efficient production of seeds capable of growing male fertile $F_1$ hybrid *Oryza sativa* plants according to claim 1 wherein said plants (ii) are generally equal or greater in height than said plants (i).

11. An improved process for the efficient production of seeds capable of growing male fertile $F_1$ hybrid *Oryza sativa* plants according to claim 1 wherein the flag leaves of said female fertile cytoplasmically male sterile plants (i) are disposed in a substantially horizontal configuration which is attributable to recessive genes.

12. An improved process for the efficient production of seeds capable of growing male fertile $F_1$ hybrid *Oryza sativa* plants according to claim 1 wherein the flag leaves of said female fertile cytoplasmically male sterile plants (i) are disposed in a decumbent configuration which is attributable to recessive genes.

13. An improved process for the efficient production of seeds capable of growing male fertile $F_1$ *Oryza sativa* plants according to claim 1 wherein the flag leaves of said female fertile cytoplasmically male sterile plants (i) are disposed in a downwardly arching configuration which is attributable to recessive genes.

14. An improved process for the efficient production of seeds capable of growing male fertile $F_1$ hybrid *Oryza sativa* plants according to claim 1 wherein the flag leaves of said female fertile cytoplasmically male sterile plants (i) are disposed in a short substantially erect configuration which is attributable to recessive genes.

15. An improved process for the efficient production of seeds capable of growing male fertile $F_1$ hybrid *Oryza sativa* plants according to claim 1 wherein at least 50 percent of the total panicle height generally extends above the maximum height of said flag leaves on said female fertile cytoplasmically male sterile rice plants (i) so that the panicles are well disposed to receive pollen from nearby plants.

16. An improved process for the efficient production of seeds capable of growing male fertile $F_1$ hybrid *Oryza sativa* plants according to claim 1 wherein said female fertile cytoplasmically male sterile rice plants (i) possess the ability to form seeds which are associated with a dominantly inherited genetic marker in the form of a straw-colored hull, and said female fertile male fertile rice plants (ii) when self-pollinated possess the ability to form seeds which are associated with a recessively inherited genetic marker in the form of a gold-colored hull.

17. An improved process for the efficient production of seeds capable of growing male fertile $F_1$ hybrid *Oryza sativa* plants according to claim 16 wherein said plants (i) possess recessively inherited light auricles and collars and said plants (ii) possess dominantly inherited dark auricles and collars.

18. An improved process for the efficient production of seeds capable of growing male fertile $F_1$ hybrid *Oryza sativa* plants according to claim 17-wherein said plants (i) possess recessively inherited substantially white auricles and collars and said plants (ii) possess dominantly inherited substantially purple auricles and collars.

19. An improved process for efficient production of seeds capable of growing male fertile $F_1$ hybrid *Oryza sativa* plants according to claim 19 which further includes a means for monitoring the purity of the desired seed product of step (d) through a determination of whether the seeds used to form plants (i) inadvertently had become contaminated with seeds which were formed on nearby maintainer plants during the formation of the planting seed used in step (a) to form plants (i) comprising:

(e) growing at least a portion of the seeds which are intended to form male fertile $F_1$ hybrid rice plants separated in step (d), and (f) determining the approximate proportion of seeds capable of forming male fertile $F_1$ hybrid rice plants present therein having dark auricles and collars in comparison to undesired seeds which form plants having light auricles and collars resulting from the continued self-pollination of maintainer plants.

20. An improved process for the efficient production of seeds capable of growing male fertile $F_1$ hybrid *Oryza sativa* plants according to claim 1 wherein said female fertile cytoplasmically male sterile rice plants (i) possess the ability to form seeds which are associated with a dominantly inherited genetic marker in the form of rudimentary glumes which are disposed over a relatively small portion of the rice hulls.

21. An improved process for the efficient production of seeds capable of growing male fertile $F_1$ hybrid *Oryza sativa* plants according to claim 1 wherein said female fertile cytoplasmically male sterile rice plants (i) and said female fertile male fertile plants (ii) additionally possess genetic markers which manifest themselves in the plant vegetation so that the identity of such parental plants can be monitored.

22. An improved process for the efficient production of seeds capable of growing male fertile $F_1$ hybrid *Oryza sativa* plants according to claim 1 wherein said female fertile male fertile plants (ii) additionally possess fully extruded anthers which are well able to disperse pollen.

23. An improved process for the efficient production of seeds capable of growing male fertile $F_1$ hybrid *Oryza sativa* plants according to claim 1 wherein said female fertile cytoplasmically male sterile rice plants (i) and said female fertile male fertile plants (ii) each possess relatively smooth leaf surfaces which are substantially incapable of retaining pollen which contacts the same.

24. An improved process for the efficient production of seeds capable of growing male fertile $F_1$ hybrid *Oryza sativa* plants according to claim 1 wherein in step (b) said pollination of said plants (i) is carried out by the wind transport of pollen from plants (ii), and said pollination of said plants (ii) is carried out by self-pollination.

25. An improved process for the efficient production of seeds capable of growing male fertile $F_1$ hybrid *Oryza sativa* plants according to claim 1--wherein said seed recovery in step (c) is carried out by use of a combine.

26. An improved process for the efficient production of seeds capable of growing male fertile $F_1$ hybrid *Oryza sativa* plants according to claim 1 wherein said seed separation in step (d) is carried out by use of photoelectric seed-sorting equipment.

27. An *Oryza sativa* seed product consisting of a substantially homogeneous assemblage of seeds which upon growth yield female fertile cytoplasmically male sterile rice plants having substantially fully exserted stigmas, panicles which are substantially fully exserted in the absence of the application of growth hormone, flag leaves which in the absence of cutting generally extend upwardly to a lesser maximum height than the tips of said panicles whereby said panicles are well disposed to receive pollen from nearby plants and the disposition of said flag leaves below the tips of said panicles is attributable to recessive genes, and the ability to form seeds which are associated with a dominantly inherited genetic marker.

28. An *Oryza sativa* seed product according to claim 27 which is capable of forming plants of the indica type.

29. An *Oryza sativa* seed product according to claim 27 which is capable of forming plants of the japonica type.

30. An *Oryza sativa* seed product according to claim 27 which is capable of forming plants wherein said flag leaves are disposed in a substantially horizontal configuration.

31. An *Oryza sativa* seed product according to claim 27 wherein said dominantly inherited genetic marker associated with the seeds is a straw-colored hull.

32. An *Oryza sativa* seed product according to claim 27 which additionally is capable of forming plants which exhibit a vegetative marker in the form of recessively inherited light auricles and collars.

33. An *Oryza sativa* seed product according to claim 32 which additionally is capable of forming plants which exhibit a vegetative marker in the form of recessively inherited substantially white auricles and collars.

34. An *Oryza sativa* seed product according to claim 27 which is capable of forming plants having substantially smooth leaf surfaces which are substantially incapable of retaining pollen which contacts the same.

35. An *Oryza sativa* seed product consisting of a substantially homogeneous assemblage of seeds which upon growth yield female fertile cytoplasmically male sterile rice plants of the indica type having substantially fully exserted stigmas, panicles which are substantially fully exserted in the absence of the application of growth hormone, flag leaves which in the absence of cutting generally extend upwardly to a lesser maximum height than the tips of said panicles whereby said panicles are well disposed to receive pollen from nearby plants and the disposition of said flag leaves below the tips of said panicles is attributable to recessive genes, the ability to form seeds which are associated with a dominantly inherited genetic marker in the form of a straw-colored hull, leaves which exhibit substantially smooth leaf surfaces which are substantially incapable of retaining pollen which contacts the same, and a vegetative marker in the form of recessively inherited substantially white auricles and collars.

36. An *Oryza sativa* seed product according to claim 35 which upon growth yields plants wherein the flag leaves are disposed in a substantially horizontal configuration.

37. Plants of *Oryza sativa* which exhibit cytoplasmic male sterility, substantially fully exserted stigmas, panicles which are substantially fully exserted in the absence of the application of growth hormone, flag leaves which in the absence of cutting generally extend upwardly to a lesser maximum height than the tips of the panicles whereby the panicles are well disposed to receive pollen from nearby plants and the disposition of said flag leaves below the tips of said panicles is attributable to recessive genes, and the ability to form seeds which are associated with a dominantly inherited genetic marker.

38. Plants of *Oryza sativa* according to claim 37 which are of the indica type.

39. Plants of *Oryza sativa* according to claim 37 are of the japonica type.

40. Plants of *Oryza sativa* according to claim 37 wherein said flag leaves are disposed in a substantially horizontal configuration.

41. Plants of *Oryza sativa* according to claim 37 which possess the ability to form seeds which are associated with a dominantly inherited genetic marker in the form of a straw-colored hull.

42. Plants of *Oryza sativa* according to claim 37 which additionally exhibit a vegetative marker in the form of recessively inherited light auricles and collars.

43. Plants of *Oryza sativa* according to claim 42 which additionally exhibit a vegetative marker in the form of recessively inherited substantially white auricles and collars.

44. Plants of *Oryza sativa* according to claim 37 which additionally possess substantially smooth leaf surfaces which are substantially incapable of retaining pollen which contacts the same.

45. Plants of *Oryza sativa* of the indica type which exhibit cytoplasmic male sterility, substantially fully exserted stigmas, panicles which are substantially fully exserted in the absence of the application of growth hormone, flag leaves which in the absence of cutting generally extend upwardly to a lesser maximum height than the tips of the panicles whereby the panicles are well disposed to receive pollen from nearby plants and the disposition of said flag leaves below the tips of said panicles is attributable to recessive genes, the ability to form seeds which are associated with a dominantly inherited genetic marker in the form of a straw-colored hull, leaves having substantially smooth leaf surfaces which are substantially incapable of retaining pollen which contacts the same, and a vegetative marker in the form of recessively inherited substantially white auricles and collars.

46. Plants of *Oryza sativa* according to claim 45 which exhibit flag leaves which are disposed in a substantially horizontal configuration.

* * * * *